Figure 1A:
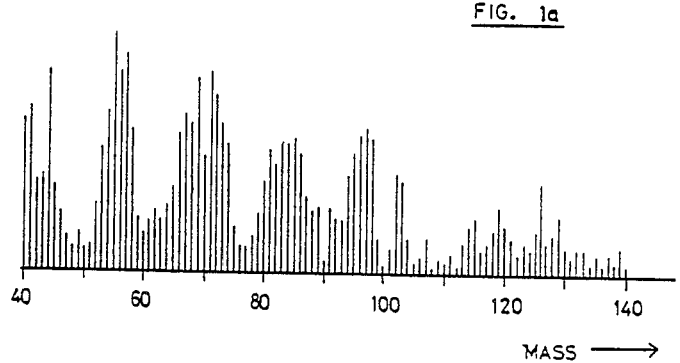

United States Patent [19]

Ottley

[11] Patent Number: 4,758,509
[45] Date of Patent: Jul. 19, 1988

[54] MICROBE GROWTH DETECTION

[75] Inventor: Thomas W. Ottley, Framfield, England

[73] Assignee: Prutec Limited, London, England

[21] Appl. No.: 849,509

[22] PCT Filed: Jul. 18, 1985

[86] PCT No.: PCT/GB85/00321
§ 371 Date: Mar. 17, 1986
§ 102(e) Date: Mar. 17, 1986

[87] PCT Pub. No.: WO86/00921
PCT Pub. Date: Feb. 13, 1986

[30] Foreign Application Priority Data

Jul. 20, 1984 [GB] United Kingdom ............... 8418515

[51] Int. Cl.⁴ .............................................. C12Q 1/02
[52] U.S. Cl. .......................................... 435/29; 435/4; 435/34; 435/39
[58] Field of Search ....................... 435/29, 34, 4, 39

[56] References Cited

U.S. PATENT DOCUMENTS 3,891,508 6/1975 Merrick .

FOREIGN PATENT DOCUMENTS 7803169 8/1979 France .

OTHER PUBLICATIONS

Risby et al.-J. Physical Chem., vol. 80, (1976), pp. 2839–2845.
Anhalt et al.-Analytical Chemistry, vol. 47, (Feb. 1975) pp. 219–224.
Windig et al.-Chem. Abst., vol. 98, (1983), p. 13934f.
Wieten et al.-Chem. Abst., vol. 101, (1984), p. 3497g.

Primary Examiner—Sam Rosen
Attorney, Agent, or Firm—Lewis Messulam

[57] ABSTRACT

A method of detection of microbial growth which comprises preparing a culture of an organism, analysing a portion taken from the whole culture in a pyrolysis mass spectrometer, and monitoring the relative height of the peak in the mass spectrum corresponding to mass of 60 daltons, an increased height of the said peak relative to the remainder of the spectrum being indicative of growth of the microorganism.

1 Claim, 1 Drawing Sheet

MICROBE GROWTH DETECTION

The present invention relates to the detection of microbial growth.

There is often a requirement in microbiology to detect the growth of micro-organisms. Examples of this are food spoilage detection and anti-microbial susceptibility testing. In the latter example, a culture is prepared of an unknown organism and small quantities of antibiotic are added to determine the concentration required to prevent growth.

It is clearly important to be able to detect the growth as quickly as possible and various methods for doing so have already been applied or proposed. For example, measurement of optical density works well where the culture medium is itself reasonably transparent. Other proposed techniques include measurement of the circular polarisation of transmitted radiation, measurement of the capacitance beween two plates placed in the medium and measurement of conductivity using two electrodes immersed in the medium.

The present invention seeks to provide a method capable of detection of microbial growth at an earlier stage than the methods previously proposed.

In accordance with a first aspect of the present invention, there is provided a method of detection of microbial growth which comprises preparing a culture of an organism, analysing a portion taken from the whole culture in a pyrolysis mass spectrometer, and monitoring the relative height of the peak in the mass spectrum corresponding to a mass of 60 daltons, an increased height of the said peak relative to the remainder of the spectrum being indicative of growth of the micro-organism.

In accordance with a second aspect of the present invention, there is provided a pyrolysis spectrometer for enabling the growth of micro-organisms to be detected which mass spectrometer is tuned or constructed to provide a first signal corresponding only to the abundance of ions present having a mass of 60 daltons and a second signal corresponding to the abundance of ions at one or more of the masses, the relative magnitude of the first and second signals being indicative of microbial growth.

Figure 1B:
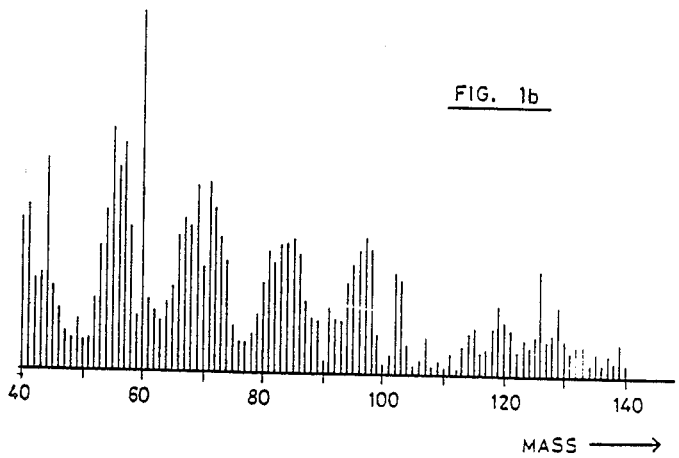

The invention will now be described further, by way of example, with reference to the accompanying drawings in which;

FIG. 1a is a typical pyrolysis mass spectrum of a bacterial culture in the absence of growth, and FIG. 1b is a similar culture to 1a after four hours of growth.

To detect microbial growth, a liquid culture is prepared in the usual manner. A typical medium may comprise 15 mls of blood diluted in 85 mls of brain-heart infusion. The broth is kept shaken at a constant 37° C., whereupon any micro-organism present should grow. To assess antibiotic susceptibility of the growing organisms, multiple cultures are prepared and several dilutions of various antibiotics are added. For example, in the case of the suspected presence of Staphylococcus aureus, it may be necessary to test for sensitivity to penicillin, tetracycline and chloramphenicol at dilutions ranging from 1 to 100 $\mu$g/ml.

After a time interval of, say, 4 hours, about 10 ul of the broth are extracted from each culture and analyised by means of a mass spectrometer. For example, the extracted broth from each flask is used to coat a ferromagnetic foil or wire to be used as sample carrier. Suitable apparatus for handling such sample carriers is described in detail in United Kingdom Patent Appln. Ser. No. 8315956 now Published Specification No. 2,141,230.

Typically a small foil of nickel/iron alloy is coated with the said culture and dried for 1 hour in a vacuum dessicator or by using a stream of hot air for about 1 minute. The foil is inserted in small glass tube which is then evacuated in the inlet system of the mass spectrometer. An r.f. induction heater outside the glass tube is used to heat the foil to its Curie point temperature. For a 50:50 nickel/iron alloy this corresponds to 510° C. At this temperature, pyrolysis of the components of the culture occurs and the molecular weights of the products are analysed by means of the deflection or filter system of the mass spectrometer.

The resulting spectra in the absence and in the presence of microbial growth are shown in FIGS. 1a and 1b, respectively. It has been found, rather surprisingly, that the only signicant change which occurs in the case of microbial growth is a significant increase in the peak at the mass of 60 daltons. Equally surprising has been the discovery that the mass 60 peak is very general and can be used to detect the growth of a wide range of micro-organisms growing in a variety of culture media. For example Escherichia coli, Pseudomonas aeruginosa, Klebsiella edwardsi, Staphylococcus aureus and Streptococcus spp all produce a significant mass 60 peak in the pyrolysis mass spectrometer after only a few hours culture in the nutrient broth.

The ions responsible for this molecular weight may be from a metabolite produced by the actively growing organisms or is may be acetic acid or another aliphatic acid or a derivative thereof. It is significant to note, however, that there are few other observable changes in the mass spectrum caused by such growth.

It is not necessary to extract the cells from the culture medium for analysis and indeed this is not desirable as it has been found that the relative signal of mass 60 is increased if the cells are not extracted from the cultrue medium.

The experimental results achieved by the use of the method of the invention correlate well with other methods such as optical density measurement. The sensitivity, however, is much higher thereby allowing detection of growth at an earlier stage. This allows, for example, a suitable antibiotic to be chosen more quickly, this having obvious benefits to the patient in clincial situations.

The particular mass spectrometer used in the anaylsis may be one capable of analysing the full spectrum but because of the restricted mass range of interest in the present invention, it will be sufficient for the spectrometer to be set to detect only the ions at this mass.

A particularly preferred construction of the mass spectrometer may comprise a magnetic sector spectrometer fitted with two collectors. Using a fixed magnetic field, the mass spectrometer may detect ions of mass 60 with one collector and ions of a slightly higher or lower molecular weight may be detected by the use of second collector. The ratio of ion currents then provides an indication of the mass 60 ionic content, the reading that the second mass being used to correct for variations caused by sample volume, that is to say for normalisation of the results.

What is claimed is:

1. A method of detection of microbial growth which comprises preparing a culture of an organism, and analysing a portion taken from the whole culture in a pyrolysis mass spectrometer, wherein the improvement comprises monitoring and comparing the relative height of the peak in the mass spectrum corresponding to a mass of 60 daltons, whereby an increased height of the said peak relative to the remainder of the spectrum is indicative of growth of the micro-organism.

* * * * *